US00PP36618P2

(12) United States Plant Patent
Erhart

(10) Patent No.: US PP36,618 P2
(45) Date of Patent: Apr. 22, 2025

(54) ***HIBISCUS* PLANT NAMED 'WALHIECLI'**

(50) Latin Name: ***Hibiscus paramutabilis* x *syriacus***
Varietal Denomination: WALHIECLI

(71) Applicant: Walberton Plants Limited

(72) Inventor: Eva Erhart, Walberton (GB)

(73) Assignee: Walburton Plants Limited (GB)

( * ) Notice: Subject to any disclaimer, the term of this patent is extended or adjusted under 35 U.S.C. 154(b) by 0 days.

(21) Appl. No.: 18/670,959

(22) Filed: May 22, 2024

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

(56) References Cited

PUBLICATIONS https://online.plantvarieties.eu/publicConsultationDetails?registerId=20241015&denomination=WALHIECLI (Year: 2024).*

* cited by examiner

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of *Hibiscus* plant named 'WALHIECLI' is disclosed, characterized by large, purple (RHS N75A) flowers with a dark red-purple (RHS 59A) eye. Plants are observed winter-hardy to −10 degrees Celsius and heat tolerant to 40 Celsius without adverse effect. Growth habit is broadly upright and spreading more with age. The new variety is a *Hibiscus*, typically produced as an outdoor ornamental plant.

2 Drawing Sheets

Latin name of the genus and species: *Hibiscus paramutabilis* x *syriacus*.

Variety denomination: 'WALHIECLI'.

BACKGROUND OF THE INVENTION

The new *Hibiscus* cultivar is a product of a planned breeding program by the inventor. *Hibiscus* 'WALHIECLI' is the result of the crossing of the seed parent, *Hibiscus* '04S43', and the pollen parent, *Hibiscus* '04S84', unpatented proprietary seedlings from the breeder's own program. The crossing resulting in this new variety was made during 2004 at a nursery in Walberton, United Kingdom.

The new cultivar was found and selected by the inventor in a group of seedlings at the same nursery in Walberton, United Kingdom during 2005.

Asexual reproduction of the new cultivar 'WALHIECLI' was first performed in July of 2019 in Walberton, United Kingdom, by softwood cuttings. Subsequent propagation has shown that the unique features of this cultivar are stable and reproduced true to type in successive generations.

SUMMARY OF THE INVENTION

The cultivar 'WALHIECLI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WALHIECLI'. These characteristics in combination distinguish 'WALHIECLI' as a new and distinct *Hibiscus* cultivar:

1. Large purple (RHS N75A) flowers with a dark red-purple (RHS 59A) eye.
2. Broadly upright habit.
3. Winter hardiness observed to at least −10° C.

PARENT COMPARISONS

Details of the parent varieties are not available for comparisons. The breeder has no records beyond the proprietary code names used in the crossing.

COMMERCIAL COMPARISONS

Plants of 'WALHIECLI' are similar in some horticultural characteristics to the variety *Hibiscus* 'WALHIROSMO', U.S. Plant Pat. No. 24,936. The new variety, however, differs in the following:

1. Petals of the new variety overlap, while petals of this comparator do not overlap.
2. Flowers of the new variety have a larger eye than flowers of this comparator.

Plants of 'WALHIECLI' are similar in some horticultural characteristics to the variety *Hibiscus* 'Woodbridge', unpatented. The new variety, however, differs in the following:

1. Flowers of the new variety are larger than flowers of this comparator.
2. Petals of the new variety overlap, while petals of this comparator do not overlap.
3. Flowers of the new variety have a much larger red eye than this comparator.

BRIEF DESCRIPTION OF THE PHOTOGRAPHS

The accompanying drawing.

Figure 1:
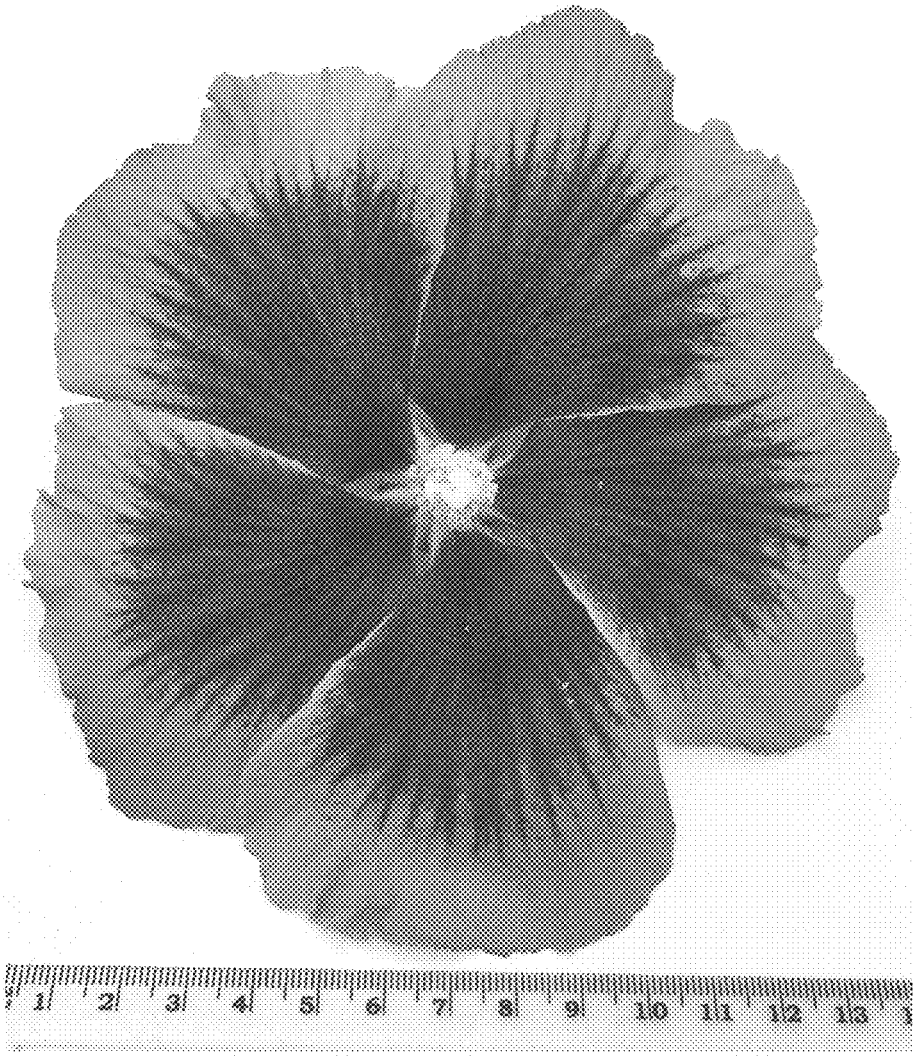
FIG. 1 illustrates in full color a typical flower from a typical plant of 'WALHIECLI' grown in an unheated glasshouse at a nursery in Walberton, United Kingdom. This plant producing this flower is approximately 3 years old.
Figure 2:
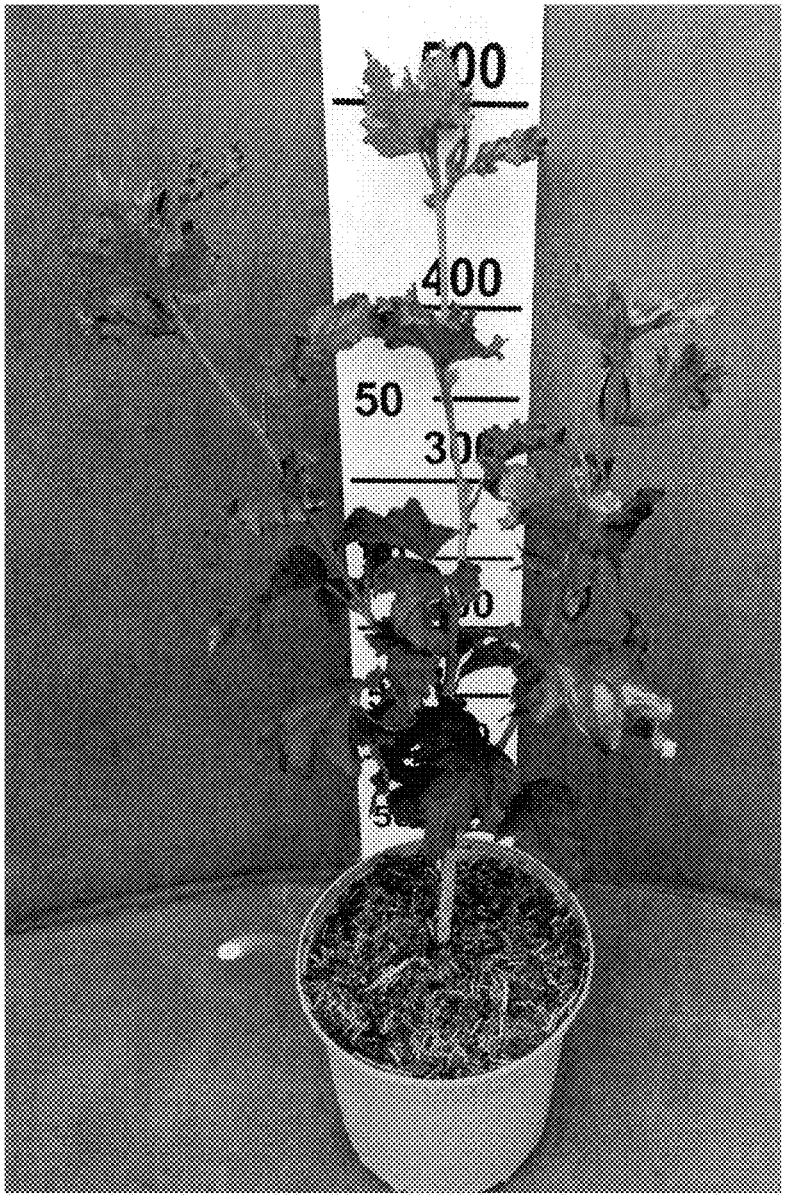
FIG. 2 illustrates a plant of about 1-year old during May, just before flowering begins.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'WALHIECLI' plant. This plant is approximately 3 years old, shown in a 6-liter container. Temperatures ranged from 0° C. to 33° C. during the day to −8° C. to 18° C. at night. No artificial light, photoperiodic treatments were given to the plants. Measurements and numerical values represent averages of typical plant types.

Botanical classification: *Hibiscus paramutabilis* x *syriacus* 'WALHIECLI'.

PROPAGATION

Time to initiate roots: 20 to 24 days in summer; 14 to 18 weeks in winter at 0° C. to 33° C.

Root description: Fine, fibrous.

PLANT

Plant type: Deciduous flowering shrub.

Age of plant described: 3 years old.

Growth habit: Broadly upright, spreading slightly with age.

Growth rate: Moderate.

Height: 85 cm.

Plant spread: 90 cm.

Branching characteristics:

Primary lateral branches:

- *Quantity*.—Typically 6 to 9.
- *Length*.—45 to 55 cm.
- *Diameter*.—0.6 cm, tapering to 0.3 cm near apex.
- *Shape*.—Virgate, upright, compact; outwardly spreading in maturity.
- *Strength*.—Stiff, strong.
- *Color*.—RHS Yellow-Green N144A, fading to between 146A and 146B on mature wood.
- *Pubescence*.—Verruscose.

Internode length: 4 to 4.5 cm.

FOLIAGE

Leaf:

- *Arrangement*.—Alternate, spirally arranged, dextrose; leaves held singly, sometimes in 2s or 3s at lower (older) nodes.
- *Quantity*.—16 to 28 per branch.
- *Average length*.—8.7 cm.
- *Average width*.—8.8 cm.
- *Shape of blade*.—Palmatifid, three-lobed.
- *Apex*.—Acute.
- *Base*.—Broadly cuneate to hastate.
- *Margin*.—Serrate, teeth 0.3 to 0.5 cm deep.
- *Texture of top surface*.—Areolate, hispid.
- *Texture of bottom surface*.—Areolate, more sparsely hispid than upper surface.
- *Color*.—Young foliage upper side: Between RHS Yellow-Green 144A and 144B. Young foliage under side: RHS Yellow-Green 144B. Mature foliage upper side: Between RHS Green NN137A and Yellow-Green 147A. Mature foliage under side: RHS Yellow-Green 147B. Autumn color upper side: RHS Orange-Yellow 19A. Autumn color under side: RHS Yellow-Orange 14C.
- *Venation*.—Type: Palmate. Venation color, upper side: RHS Green NN137C. Venation color, under side: RHS Yellow-Green 144B.
- *Petiole*.—Length: 1.7 to 1.9 cm. Diameter: 0.25 cm. Color: RHS Green 137C. Texture: Sparsely tomentose to pillose.

FLOWER

Natural flowering season: May to September in Walberton, UK.

Flower type and habit: Single, rotate, overlapping.

Rate of flower opening: 2 to 3 days from bud dehiscence (cracking color) to fully opened flower.

Flower longevity on plant: 2 to 3 days.

Persistence: Persistent.

Fragrance: Very weak.

Bud:

- *Shape*.—Ovate.
- *Length*.—1.5 cm.
- *Diameter*.—1 cm.
- *Apex*.—Acute to attenuate.
- *Base*.—Rounded.
- *Texture*.—Scabrid to verrucose.
- *Color*.—RHS Yellow-Green 147C and 147D.

Flower size:

- *Diameter*.—14 cm.
- *Depth*.—4.5 cm.

Petals:

- *Quantity*.—5.
- *Arrangement*.—Rotate.
- *Length*.—6.5 to 7 cm.
- *Width*.—6.5 cm at widest.
- *Shape*.—Orbicular to obovate.
- *Apex*.—Rounded.
- *Base*.—Obtuse.
- *Margin*.—Entire to slightly serrate at the sides; medium crenate, undulate at the outer edges.
- *Texture, upper and lower surfaces*.—Glabrous, shiny.
- *Color*.—Eye — size and feathering: Extends 70% to 75% of length of petal from petal base, low feathering. When opening, upper surface, main color: RHS Purple N78B and N78C. When opening, upper surface, eye color: RHS Greyed-Purple 187B at center, fading to 187D near edge of eye. When opening, lower surface: Between RHS Red-Purple N74D and 75A, veins White155A. Fully opened, upper surface, main color: RHS Purple N75A. Fully opened, upper surface, eye color: RHS Red-Purple 59A, fading to 59C near the edge of the eye. Fully opened, lower surface: RHS Purple 75A; veins White 155A; base of petal between White 155A and 155B.

Calyx sepals:

*Quantity.*—5.

*Length.*—2.4 to 3.0 cm.

*Width.*—1.2 to 1.3 cm at widest part.

*Shape* (*overall*).—Broadly lanceolate, campanulate. Apex: Acute to attenuate. Base: Truncate, fused.

*Margin.*—Entire.

*Color.*—Upper and lower surfaces RHS Yellow-Green N148A and N148B, fading to N148C at base.

*Texture.*—Strigose to scabrid.

Epicalyx sepals:

*Quantity.*—4 to 7, usually 5 or 6.

*Length.*—2.3 to 2.5 cm.

*Width.*—0.4 to 0.5 cm at widest part.

*Shape* (*overall*).—Linear-lanceolate, fused at base; upper third tortuous; campanulate overall.

*Apex.*—Acute to attenuate.

*Base.*—Truncate.

*Margin.*—Entire.

*Color.*—RHS Yellow-Green 147D at base, fading to 147B at apex.

*Texture.*—Strigose to scabrid.

Peduncle:

*Length.*—1.3 cm.

*Diameter.*—0.4 to 0.5 cm.

*Angle.*—45° to 60° to the lateral branch.

*Strength.*—Strong, rigid.

*Texture.*—Scabrid to verrucose.

*Color.*—RHS Yellow-Green 147B.

REPRODUCTIVE ORGANS

Stamen stalk:

*Length.*—2.9 cm.

*Diameter.*—0.5 cm at base, tapering to 0.25 cm near apex.

*Color.*—RHS White NN155D, with short vertical stripes of RHS Red-Purple 63B, the stripes aligned with the center of the petals and extending 0.6 cm from the base.

*Protruding beyond petals.*—Yes, in fully opened flowers.

Stamens:

*Quantity.*—Typically between 60 and 75.

*Arrangement on stalk.*—5 to 6 whorls.

Anthers:

*Shape.*—Globular.

*Length.*—Approximately 0.15 to 0.2 cm.

*Color.*—RHS Greyed-Yellow 162C and 162D.

*Pollen.*—Color: RHS Yellow 9C. Quantity: Very little.

Pistil:

*Number.*—5.

*Length.*—0.4 cm.

*Style.*—Length: 0.26 cm. Color: White 155A.

*Stigma.*—Shape: Lanceolate. Color: White 155A. Ovary Color: RHS Yellow-Green 149D.

OTHER CHARACTERISTICS

Seeds: Not observed.

Disease/pest resistance: Neither resistance nor susceptibility to normal diseases and pests of *Hibiscus paramutabilis* x *Hibiscus syriacus* have been observed.

Temperature tolerance: Trialed without adverse effect at temperatures ranging −10° C. to 40° C.

What is claimed is:

1. A new and distinct cultivar of *Hibiscus* plant named 'WALHIECLI' as herein illustrated and described.

* * * * *

1
2
3
4
5
6
7
8
9
10
11
12
13